US00PP23569P3

(12) United States Plant Patent
Radler

(10) Patent No.: US PP23,569 P3
(45) Date of Patent: Apr. 30, 2013

(54) SHRUB ROSE PLANT NAMED 'RADSOUTH'

(50) Latin Name: *Rosa hybrida*
Varietal Denomination: Radsouth

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 13/137,230

(22) Filed: Jul. 29, 2011

(65) Prior Publication Data

US 2013/0031681 P1 Jan. 31, 2013

(51) Int. Cl.
*A01H 5/00* (2006.01)

(52) U.S. Cl. ..... Plt./107

(58) Field of Classification Search ..... Plt./107
See application file for complete search history.

*Primary Examiner* — Kent L Bell

(74) *Attorney, Agent, or Firm* — Buchanan Ingersoll & Rooney

(57) ABSTRACT

A new and distinct shrub rose plant is provided that abundantly and substantially continuously forms attractive single pink blossoms. The plant exhibits vigorous vegetation and a mounding and bushy growth habit. The ornamental foliage is dark green with a semi-glossy finish. Good resistance to blackspot has been experienced. The plant is well suited for growing as attractive ornamentation in parks and gardens.

1 Drawing Sheet

Botanical/commercial classification: *Rosa hybrida*/Shrub Rose Plant.

Varietal denomination: cv. Radsouth.

SUMMARY OF THE INVENTION

The new variety of *Rosa hybrida* landscape shrub rose plant of the present invention was created during 2002 at Greenfield, Wis., U.S.A., by artificial pollination wherein two parents were crossed which previously had been studied in the hope that they would contribute the desired characteristics. The female parent (i.e., the seed parent) was the 'Radrise2' variety (non-patented in the United States). The male parent (i.e., the pollen parent) of the new variety was the 'Radcor' variety (U.S. Plant Pat. No. 17,346). The parentage of the new variety can be summarized as follows:

'Radrise2'×'Radcor'.

The seeds resulting from the above pollination were sown and small plants were obtained which were physically and biologically different from each other. Selective study resulted in the identification of a single plant of the new variety.

It was found that the new Landscape Shrub rose plant of the present invention possesses the following combination of characteristics:

(a) abundantly and substantially continuously forms attractive single pink blossoms,
(b) exhibits a mounding and bushy growth habit,
(c) forms vigorous vegetation,
(d) forms attractive ornamental dark green foliage with a semi-glossy finish, and
(e) exhibits excellent resistance to blackspot.

A new rose variety is provided which bears attractive single pink blossoms combined with substantially continuous blooming and blackspot resistance.

The new variety well meets the needs of the horticultural industry. It can be grown to advantage as ornamentation in parks, gardens, public areas, and in residential settings. The new variety is particularly well suited for providing attractive ornamentation in the landscape. The pink blossom color contrasts nicely with the semi-glossy dark green foliage.

The new variety of the present invention also can be readily distinguished from its ancestors. More specifically, the 'Radcor' variety displays lighter coral pink blossoms, with a strong yellow center, while the blossoms of the new variety are darker pink with a slight cream to yellow center. The 'Radrise2' variety displays larger blossoms that are lighter in color and a climbing growth habit unlike the new variety. The new variety of the present invention also can be readily distinguished from the 'Radcon' variety (U.S. Plant Pat. No. 15,070) upon an inspection of the blossoms. More specifically, the blossoms of the new variety are considerably darker pink than those of the 'Radcon' variety.

Additionally, the new variety can be readily distinguished from the 'Radrazz' variety (U.S. Plant Pat. No. 11,836) and the 'Meipotal' variety (U.S. Plant Pat. No. 8,841) upon an inspection of the blossom color. The blossoms of the 'Radrazz' variety are cherry red in coloration, and those of the 'Meipotal' variety are pink with white eyes.

The characteristics of the new variety have been found at Wasco, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radsouth'.

BRIEF DESCRIPTION OF THE PHOTOGRAPH

The accompanying photograph shows, as nearly true as it is reasonably possible to make the same in a color illustration of this character, a row of typical flowering plants of the new variety. The illustrated rose plants of the new variety were approximately two years of age and were observed during June while growing outdoors near West Grove, Pa., U.S.A.

DETAILED DESCRIPTION

The chart used in the identification of colors is that of The Royal Horticultural Society (R.H.S. Colour Chart), London, England. The description is based on the observation of two-year-old specimens of the new variety during June while growing outside on their own roots near West Grove, Pa., U.S.A.

Class: Landscape Shrub.

Plant:

*Height*.—Approximately 2.5 feet on average at the end of the growing season.

*Width*.—Approximately 4 feet on average at the end of one growing season.

*Habit*.—Mounding and bushy.

Branches:

*Color*.—Near Yellow-Green Group 145A for young branches, near Yellow-Green Group 144A on mature branches, and commonly with some patches of Greyed-Orange Group 165A on the oldest branches.

*Main branches*.—Commonly up to approximately 5 mm in diameter.

*Secondary branches*.—Commonly up to approximately 3 mm in diameter.

*Texture*.—Glabrous on young branches and mostly glabrous with some roughness on older branches.

*Thorns*.—Size: approximately 1 cm in length perpendicular to the stem, approximately 5 mm in width parallel to the stem, near Yellow-Green Group 151D in coloration when young, and near Greyed-Orange Group 166B when fully mature.

Leaves:

*Size*.—A five-leaflet leaf commonly is approximately 10 cm in length on average, and approximately 7.5 cm in width on average.

*Leaflets*.—Number: 3, 5, and 7. length: approximately 4.5 cm on average for a terminal leaflet, and approximately 3 cm on average for a lower leaflet. width: approximately 3 cm on average for a terminal leaflet, and approximately 2 cm on average for a lower leaflet. shape: ovate with a rounded base and an acuminate tip. margins: serrate. texture: smooth on both surfaces and somewhat rough around the midrib on the under surface. overall appearance: attractive dark green semi-glossy leaves. color: upper surface: near Green Group 137A. under surface: near Green Group 138B.

*Petioles*.—Near Yellow-Green Group 144A in coloration, commonly approximately 2 cm in length on average and approximately 1 mm in diameter on average, and smooth with occasional small thorns that are approximately 1 mm in length.

*Petiolules*.—Near Red-Purple Group 61A in coloration, commonly approximately 2 mm in length on average and approximately 1 mm in diameter, and smooth in texture.

*Stipules*.—Near Green Group 137C in coloration, commonly approximately 1.2 cm in length on average and approximately 3 mm in width on average, and smooth in texture.

Inflorescence:

*Number of flowers*.—Commonly approximately 6 or 7 blooms on average in a cluster.

*Peduncle*.—Near Yellow-Green Group 145A in coloration, commonly approximately 6 mm in length, and approximately 2 mm in diameter, and commonly smooth covered with short hairs having lengths less than 1 mm.

*Sepals*.—Shape: generally lanceolate with a caudate apex and an entire margin. upper surface: soft and very tomentose, and commonly Yellow-Green Group 145A in coloration. under surface: generally smooth, and Yellow-Green Group 145A in coloration. size: commonly approximately 2.5 cm in length on average, and approximately 0.8 cm in width at the base. number: five.

*Buds*.—Shape: generally ovoid. length: approximately 2 cm on average as the calyx breaks. diameter: approximately 1 cm as the calyx breaks. color: near Red-Purple Group 57A when opening.

*Flower*.—Form: single. diameter: approximately 7 cm on average when fully open.

*Height*.—Approximately 3.5 cm when fully open. color: upper surface: near Red-Purple Group 57B with Yellow Group 2D at the point of attachment. under surface: near Red-Purple Group 57C with Yellow Group 2D at the point of attachment. fragrance: none noticeable. petal number: commonly approximately 7 or 8 on average under normal growing conditions. petal shape: broadly obcordate. petal apex: emarginate. petal length: commonly approximately 4.2 cm on average. petal width: commonly approximately 4 cm on average at widest point. petal margin: entire with reflex to provide a wavy appearance. petal texture: smooth on both surfaces. petal drop: the petals commonly detach cleanly and freely drop upon maturity. stamen number: approximately 80 to 90 on average, and regularly arranged about the pistils. anthers: approximately 3 mm in length on average, approximately 2 mm in width on average, and Greyed-Orange Group 163A in coloration. pollen: commonly present in a moderate quantity, and near Yellow-Orange Group 22A in coloration. filaments: approximately 5 to 10 mm in length, and Orange-Red Group 33B in coloration. pistils: separate and free, and commonly number approximately 50 to 60 on average. styles: commonly approximately 8 mm in length on average, near Red-Purple Group 58D on the upper ⅔s, and near Yellow Group 11D on the lower ⅓. stigmas: commonly near 1 mm in diameter, and near Yellow Group 11D in coloration. receptacle: commonly substantially spherical in shape, approximately 8 mm in length on average, approximately 7 mm in width on average, glabrous, near Yellow-Green Group 144A in coloration; and achenes commonly are present on the bottom and wall. hips: generally rotund in shape, approximately 1 cm in length on average, approximately 1.5 cm in diameter on average, and commonly near Green Group 137A in coloration. seeds: generally oval in shape, approximately 5 mm in length on average, approximately 4 mm in diameter on average, and commonly near Greyed-Yellow Group 161B in coloration.

Development:

*Vegetation*.—Vigorous and strong.

*Blossoming*.—Abundant and substantially continuous during the growing season.

*Resistance to diseases*.—Good with respect to black-spot, mildew, and rust.

Plants of the 'Radsouth' variety have not been observed under all possible environmental conditions to date. Accordingly, it is possible that the phenotypic expression may vary somewhat with changes in light intensity and duration, cultural practices, and other environmental conditions.

I claim:

1. A new and distinct Landscape Shrub rose plant characterized by the following combination of characteristics:

(a) abundantly and substantially continuously forms attractive single pink blossoms, (b) exhibits a mounding and bushy growth habit, (c) forms vigorous vegetation, (d) forms attractive ornamental dark green foliage with a semi-glossy finish, and (e) exhibits excellent resistance to blackspot;

substantially as herein shown and described.

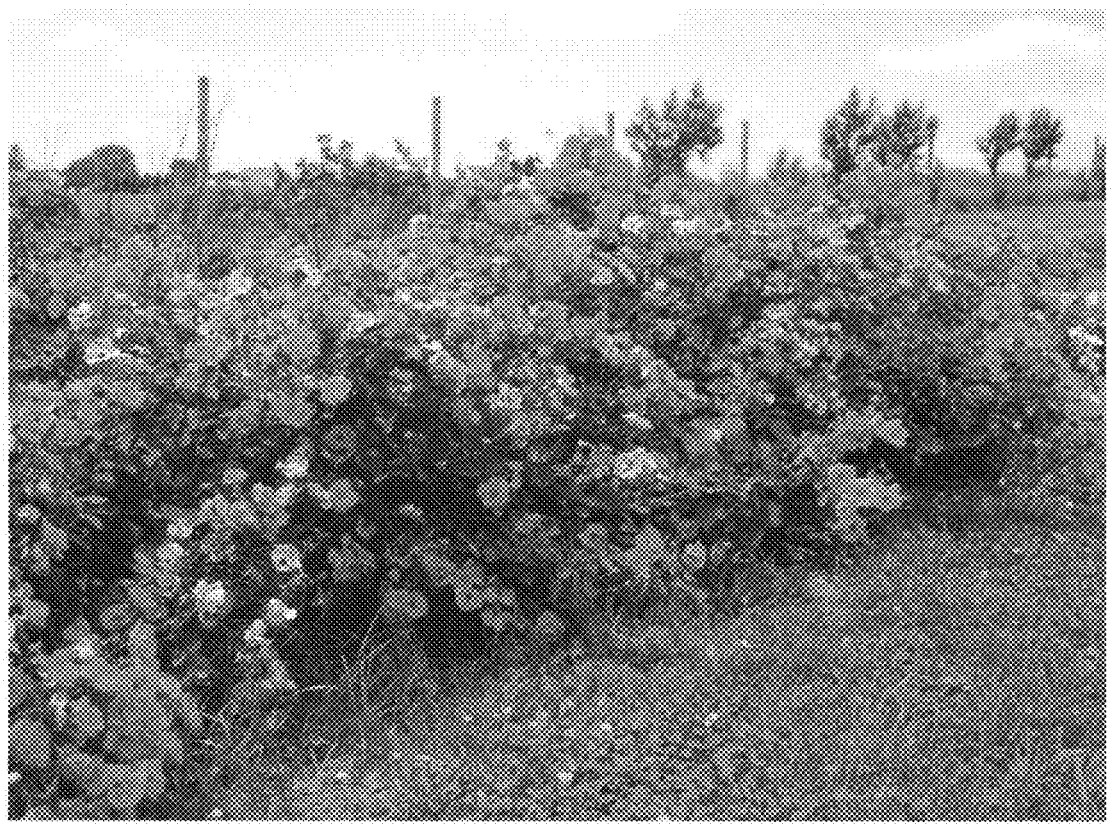

* * * * *